United States Patent [19]

Grisar et al.

[11]  4,255,575
[45]  Mar. 10, 1981

[54] 2-HYDROXY-5-(1-HYDROXY-2-PIPERAZINYLETHYL)-BENZOIC ACID DERIVATIVES

[75] Inventors: J. Martin Grisar; George P. Claxton, both of Cincinnati, Ohio

[73] Assignee: Richardson-Merrell Inc., Wilton, Conn.

[21] Appl. No.: 36,244

[22] Filed: May 4, 1979

[51] Int. Cl.$^3$ .................. C07D 295/08; C07D 401/04
[52] U.S. Cl. .................................. 544/394; 544/360; 424/250
[58] Field of Search ............................. 544/394, 360

[56] References Cited

U.S. PATENT DOCUMENTS

| | | | |
|---|---|---|---|
| 3,856,794 | 12/1974 | Danilewicz et al. | 544/394 |
| 4,038,279 | 7/1977 | Renth et al. | 544/394 |

*Primary Examiner*—Jose Tovar
*Attorney, Agent, or Firm*—William J. Stein; George W. Rauchfuss, Jr.

[57] ABSTRACT

Derivatives of 2-hydroxy-5-(1-hydroxy-2-piperazinylethyl)benzoic acid are prepared which are useful for their blocking action on α and β-adrenergic receptors. In addition, these compounds are useful as spasmolytic and antihypertensive agents.

6 Claims, No Drawings

2-HYDROXY-5-(1-HYDROXY-2-PIPERAZINYLETHYL)-BENZOIC ACID DERIVATIVES

DESCRIPTION

FIELD OF THE INVENTION

This invention relates to 1-hydroxy-2-piperazinylethyl derivatives of benzoic acid and their preparation.

SUMMARY OF THE INVENTION

This invention relates to novel derivatives of 2-hydroxy-5-(1-hydroxy-2-piperazinylethyl)benzoic acid. More particularly, this invention relates to certain 2-hydroxy, 2-methoxy and 2-ethoxy derivatives of 5-(1-hydroxy-2-piperazinylethyl)benzoic acid or benzamide. Still more particularly, this invention relates to derivatives of 2-hydroxy-5-(1-hydroxy-2-piperazinylethyl)-benzoic acid having the general formula:

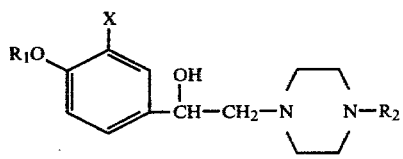

wherein X is selected from the group consisting of carboxy, carbomethoxy, carboxamide, N-alkylcarboxamide in which the alkyl group has from 1 to 12 carbon atoms, N,N-dimethylcarboxamide, N,N-diethylcarboxamide and 5-tetrazolyl; $R_1$ is hydrogen, methyl and ethyl; $R_2$ is selected from the group consisting of phenyl, substituted phenyl, 2-pyridyl and substituted-2-pyridyl in which said substitution in lower alkyl and lower alkoxy having from 1 to 4 carbon atoms, fluorine, chlorine and trifluoromethyl; and the pharmaceutically acceptable acid addition salts thereof.

This invention further discloses a method whereby these derivatives may be conveniently prepared in good yield.

DETAILED DESCRIPTION OF THE INVENTION

As seen in general formula (I) above, all of the compounds of this invention contain a 1-hydroxy-2-piperazinylethyl moiety attached to the 5-position of the phenyl ring. The remaining two variable groups attached to the phenyl ring, as represented by the symbol X and $R_1$, can include the carboxyl and hydroxyl groups, respectively. Thus, for purposes of uniformity of nomenclature, all of the compounds described herein are designated as 2-hydroxy-5-(1-hydroxy-2-piperazinylethyl) derivatives of benzoic acid.

In addition to the various derivatives of benzoic acid described herein, the corresponding methyl ester and certain amides are also contemplated as within the scope of this invention. Thus, where the symbol X represents the carbomethoxy group the methyl 2-hydroxy-5-(1-hydroxy-2-piperazinylethyl)benzoates are contemplated.

Where the symbol X represents the carboxamide, N-alkylcarboxamide, N,N-dimethylcarboxamide or the N,N-diethylcarboxamide groups the various substituted and unsubstituted benzamides are delineated. In the case of the N-substituted benzamides, the amide nitrogen can be substituted by an alkyl group having from 1 to 12 carbon atoms. Illustrative of the N-alkyl groups are methyl, ethyl, propyl, butyl, amyl, hexyl, heptyl, octyl, nonyl, decyl, undecyl, and dodecyl. Preferably, the N-lower alkyl groups having from from 1 to 4 carbon atoms are employed. In addition, the various branched and positional isomers are included within the scope of this invention as long as the alkyl group is univalent and does not exceed a total of 12 carbon atoms. Lastly, the symbol X can represent the specific heterocycle moiety 5-tetrazolyl which yields derivatives that have excellent spasmolytic and anti-hypertensive activity.

The symbol $R_1$ is represented by hydrogen or the methyl and ethyl groups. Where $R_1$ is hydrogen and X is carboxy, the compounds can be designated as 5-(1-hydroxy-2-piperazinylethyl) derivatives of salicylic acid. However, for uniformity of nomenclature these compounds will be termed as derivatives of 2-hydroxy-5-(1-hydroxy-2-piperazinylethyl)benzoic acid.

As can be further seen in formula (I) above, the 4-position of the piperazine ring cannot remain unsubstituted and must be substituted with either a phenyl or a 2-pyridyl moiety. The phenyl or 2-pyridyl rings can remain unsubstituted or they can be mono-substituted in either of the ortho, meta or para positions of the aromatic ring. The various substituents that are contemplated include the lower alkyl, lower alkoxy, fluorine, chlorine and trifluoromethyl groups. Preferably, the lower alkyl and lower alkoxy groups are employed. Still more preferable are the o-methyl and o-methoxy groups located on the phenyl ring. The term lower alkyl and lower alkoxy refers to a monovalent radical derived from an aliphatic hydrocarbon having from 1 to 4 carbon atoms and includes such radicals as methyl, ethyl, propyl, isopropyl, butyl, isobutyl and t-butyl.

When the symbol X represents the carboxamide, N-alkylcarboxamide, N,N-dimethylcarboxamide or the N,N-diethylcarboxamide groups and the symbol $R_2$ represents a methyl or methoxy substituted phenyl group, a preferred class of benzamides is further delineated within the broad scope of the present invention.

Still further preferred are those compounds wherein the symbol X represents the primary carboxamide group and the symbol $R_2$ is an o-methyl substituted phenyl group or an o-methoxy substituted phenyl group. Such compounds are designated as 2-hydroxy(-methoxy or ethoxy)-5-[1-hydroxy-2-[4-(2-methylphenyl)-1-piperazinyl]ethyl]benzamides or 2-hydroxy(-methoxy or ethoxy)-5-[1-hydroxy-2-[4-(2-methoxyphenyl)-1-piperazinyl]ethyl]benzamides.

The expression pharmaceutically acceptable acid addition salts encompasses any non-toxic organic or inorganic acid addition salts of the base compounds represented by formula (I). Illustrative inorganic acids which form suitable salts are hydrochloric, hydrobromic, sulfuric and phosphoric acid as well as acid metal salts such as sodium monohydrogen orthophosphate and potassium hydrogen sulfate. Illustrative organic acids which form suitable salts include the mono-, di- and tri-carboxylic acids, for example, acetic, fumaric, malic, tartaric, citric, ascorbic, maleic, hydroxymaleic, benzoic, hydroxybenzoic, phenylacetic, cinnamic, salicylic, 2-phenoxybenzoic and sulfonic acids such as methane sulfonic acid and 2-hydroxyethane sulfonic acid. Either the mono- or the di-acid salts can be formed, and such salts can exist in either a hydrated or a substantially anhydrous form.

Illustrative specific free base compounds encompassed by formula (I) above include:

2-hydroxy-5-[1-hydroxy-2-(4-phenyl-1-piperazinyl)ethyl]benzoic acid,
2-ethoxy-5-[1-hydroxy-2-[4-(2-butoxyphenyl)-1-piperazinyl]ethyl]benzoic acid,
2-hydroxy-5-[1-hydroxy-2-[4-(2-pyridyl)-1-piperazinyl]ethyl]benzoic acid,
5-[1-hydroxy-2-[4-(3-chlorophenyl)-1-piperazinyl]ethyl]-2-methoxybenzoic acid,
5-[1-hydroxy-2-[4-[(3-fluoro)-2-pyridyl]-1-piperazinyl]ethyl]-2-methoxybenzoic acid,
methyl 2-hydroxy-5-[1-hydroxy-2-(4-phenyl-1-piperazinyl)ethyl]benzoate,
methyl 2-ethoxy-5-[1-hydroxy-2-[4-(3-trifluoromethylphenyl)-1-piperazinyl]ethyl]benzoate,
methyl 2-hydroxy-5-[1-hydroxy-2-[4-(2-pyridyl)-1-piperazinyl]ethyl]benzoate,
methyl 5-[1-hydroxy-2-[4-(4-propylphenyl)-1-piperazinyl]ethyl]-2-methoxybenzoate,
methyl 5-[1-hydroxy-2-[4-[(4-ethoxy)-2-pyridyl]-1-piperazinyl]ethyl]-2-methoxybenzoate,
2-hydroxy-5-[1-hydroxy-2-(4-phenyl-1-piperazinyl)ethyl]benzamide,
2-ethoxy-5-[1-hydroxy-2-[4-(2-fluorophenyl)-1-piperazinyl]ethyl]benzamide,
2-hydroxy-5-[1-hydroxy-2-[4-(2-pyridyl)-1-piperazinyl]ethyl]benzamide,
5-[1-hydroxy-2-[4-[(3-methyl)-2-pyridyl]-1-piperazinyl]ethyl]-2-methoxybenzamide,
5-[1-hydroxy-2-[4-(3-butylphenyl)-1-piperazinyl]ethyl]-2-methoxybenzamide,
2-hydroxy-5-[1-hydroxy-2-(4-phenyl-1-piperazinyl)ethyl]-N-methylbenzamide,
2-ethoxy-5-[1-hydroxy-2-[4-(2-isopropoxyphenyl)-1-piperazinyl]ethyl]-N-propylbenzamide,
2-hydroxy-5-[1-hydroxy-2-[4-(2-pyridyl)-1-piperazinyl]ethyl]-N-hexylbenzamide,
5-[1-hydroxy-2-[4-[(4-trifluoromethyl)-2-pyridyl]-1-piperazinyl]ethyl]-2-methoxy-N-nonylbenzamide,
5-[1-hydroxy-2-[4-(3-fluorophenyl)-1-piperazinyl]ethyl]-2-methoxy-N-dodecylbenzamide,
2-hydroxy-5-[1-hydroxy-2-(4-phenyl-1-piperazinyl)ethyl]-N,N-dimethylbenzamide,
2-ethoxy-5-[1-hydroxy-2-[4-(4-t-butylphenyl)-1-piperazinyl]ethyl]-N,N-dimethylbenzamide,
2-hydroxy-5-[1-hydroxy-2-[4-(2-pyridyl)-1-piperazinyl]ethyl]-N,N-diethylbenzamide,
5-[1-hydroxy-2-[4-[(3-ethoxy)-2-pyridyl]-1-piperazinyl]ethyl]-2-methoxy-N,N-diethylbenzamide, and
5-[1-hydroxy-2-[4-(3-methoxyphenyl)-1-piperazinyl]ethyl]-2-methoxy-N,N-dimethylbenzamide.

The 2-hydroxy-5-(1-hydroxy-2-piperazinylethyl)benzoic acid derivatives of formula (I) are readily prepared by condensing a derivative of 2-hydroxy-5-(2-bromoacetyl)benzoic acid (II) with a 1-(substituted)piperazine (III). The resulting 2-hydroxy-5-(2-piperazinylacetyl)benzoic acid derivative (IV) is subsequently reduced to the desired derivative of 2-hydroxy-5-(1-hydroxy-2-piperazinylethyl)benzoic acid (I). This process may be schematically illustrated as follows:

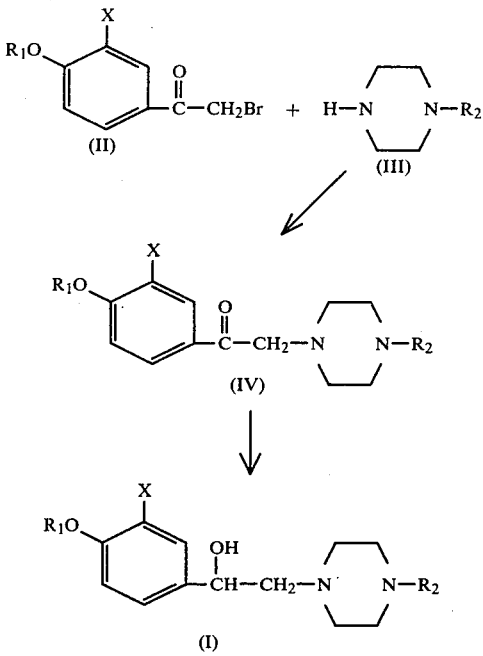

The 2-hydroxy-5-(2-bromoacetyl)benzoic acid derivatives (II) are readily obtained via the bromination of the corresponding known 2-hydroxy-5-acetyl benzoic acid derivatives. Bromination is conducted in an inert solvent such as chloroform or tetrahydrofuran by the addition of a brominating agent such as bromine, cupric bromide, pyrrolidone-2 hydrotribromide and phenyltrimethylammonium perbromide. Where the symbol X is the carbomethoxy group, the use of bromine is most convenient.

The condensation to the 2-hydroxy-5-(2-piperazinylacetyl)benzoic acid derivatives (IV) is conducted in a suitable anhydrous solvent such as diethyl ether, tetrahydrofuran or dimethylformamide. The resulting hydrobromic acid that is released is captured by the 2-hydroxy-5-(2-piperazinylacetyl)benzoic acid derivative (IV) that forms. More conveniently an equivalent of triethylamine or a base that is stronger in basicity than the desired 5-(2-piperazinylacetyl)benzoic acid derivative can be added to form a hydrobromide salt which can be readily separated.

The condensation reaction proceeds at a reasonable rate at room temperature and is slightly exothermic. Control of the reaction time and temperature is important inasmuch as the carbonyl groups present in the 2-hydroxy-5-(2-bromoacetyl)benzoic acid derivatives (II) and the 2-hydroxy-5-(2-piperazinylacetyl)benzoic acid derivatives that form (IV) can also undergo reactions with the 1-substituted piperazine, resulting in undesirable side products. The condensation can be conducted at a temperature range of from about 0° to 50° C. and for a period ranging from 1 hour to 3 days. Preferably a temperature of from 20° to 30° C. and a reaction time of from 2 to 16 hours is employed. The slow addition of the 2-hydroxy-5-(2-bromoacetyl)benzoic acid derivatives to the 1-substituted piperazine is also advantageous.

Reduction of the 2-hydroxy-5-(2-piperazinylacetyl)benzoic acid derivatives (IV) to the corresponding alcohols (I) of the present invention can be achieved using a variety of reagents. Where the symbol X is a carbomethoxy group, it is important to use a selective reducing reagent that will reduce only the ketone and not the ester function as well. The reduction can be achieved by hydrogenation in the presence of a noble metal catalyst such as platinum, palladium or rhodium on charcoal. Preferably, a palladium on charcoal catalyst is employed where hydrogenation is employed.

Alternatively, a suitable metal hydride reagent can be employed. The choice of the particular hydride reagent employed is dependent upon the nature of the symbol X. Thus, where X is the carbomethoxy group or an amide function, the reagent must be one that reduces only the desired ketone and not the carbonyl ester or amide function. Where X represents the carbomethoxy group sodium borohydride in methanol at a temperature of from 0° to 20° C. is preferably employed. In the event that a stereoselective reduction is desired, the use of certain highly hindered lithium or potassium trialkylborohydride reagents may be favorably employed, as for example lithium-B-isopinocampheyl-9-borabicyclo[3.3.1]nonyl hydride, cf., Krishnamurthy et al., J. Org. Chem., 42, 2534 (1977).

In the case where the symbol X represents a carboxy or an amide function, it may be desirable to prepare the corresponding methyl ester of the 2-hydroxy-5-(1-hydroxy-2-piperazinylethyl)benzoic acid derivative desired and subsequently hydrolyze it to the corresponding free acid or convert it to the particular amide desired. Hydrolysis of the methyl esters of (I) to the corresponding free acid can be achieved using either aqueous acid or alkali in accordance with standard procedures well known to those skilled in the art.

The conversion of the methyl esters (I) to the corresponding amides, N-substituted or N,N-disubstituted amides is conducted using an excess of ammonia or the appropriate amine in an alcoholic solvent. Preferably, methanol is employed. If a gaseous amine, such ammonia or methylamine, is employed, the reaction temperature should be maintained at 25° C. or lower, unless the reaction is conducted in a suitable closed pressurized vessel. The amide conversion reaction can be facilitated by the use of a catalyst such as sodium methoxide, sodium amide or dimethylaluminum amide (A. Basha et al., Tetrahedron Letters, 1977, pp. 4171–7). In most cases freshly prepared sodium methoxide provides satisfactory results.

The compounds of formula (I) possess $\alpha$ and $\beta$-adrenergic receptor blocking activity and are useful in the treatment or prophylaxis of cardiovascular disorders, as for example arrhythmias, coronary heart disease, angina pectoris and hypertension in mammals. In addition, these compounds possess useful spasmolytic activity in mammals. The term mammals is intended to include inter alia such mammals as mice, rats, guinea pigs, rabbits, ferrets, dogs, cats, cows, horses and primates including man.

The 2-hydroxy-5-(1-hydroxy-2-piperazinylethyl)benzoic acid derivatives can be administered as their pharmaceutical salts in combination with a pharmaceutical carrier using conventional dosage unit forms. Suitable dosage unit forms include oral preparations such as tablets, capsules, powders, granules, oral solutions and suspensions, sublingual and intrabuccal preparations, as well as parenteral dosage unit forms useful for subcutaneous intramuscular or intravenous administration.

The amount of the active ingredient to be administered can vary widely according to the particular dosage unit employed, the period of treatment, the age and sex of the patient treated and the nature and extent of the disorder treated. The total amount of active ingredient to be administered will generally range from about 1 mg/kg to 100 mg/kg and preferably from 3 mg/kg to 25 mg/kg. A unit dosage may contain from 25 to 500 mg of active ingredient, preferably from 100 to 250 mg of active ingredient, and can be taken one or more times per day.

The preferred route of administration is via oral administration. Illustrative dosage levels of the active ingredient for oral administration range from 1 to 100 mg/kg of body weight. Preferably from 3 to 25 mg/kg of the active ingredient are orally administered in humans during a 24 hour period. In those instances where the drug is administered by the parenteral route, corresponding lower dosages are usually employed.

Formulations for oral use may be presented as hard or soft shelled gelatin capsules containing only the active ingredient, but generally blended with conventional pharmaceutical carriers or excipients such as gelatin, various starches, lactose, calcium phosphate, or powdered sugar. The term pharmaceutical carrier is intended to include lubricants employed to improve the flow of tablet granulations and to prevent the adhesion of tablet material to the surfaces of tablet dies and punches. Suitable lubricants include, for example, talc, stearic acid, calcium stearate, magnesium stearate and zinc stearate. Also included in the definition of a pharmaceutical carrier as used herein are disintegrating agents added to assist the break up and dissolution of tablets following administration, dyes and coloring agents, and flavoring agents to enhance the aesthetic qualities of the tablets and make them more acceptable to the patient.

Suitable liquid excipients for the preparation of liquid dosage unit forms include water and alcohols such as ethanol, benzyl alcohol and the polyethylene alcohols, either with or without the addition of a surfactant. In general, the preferred liquid excipients include water, saline solution, dextrose and glycol solution, as for example an aqueous propylene glycol or an aqueous solution of polyethylene glycol. Liquid preparations to be used as sterile injectable solutions will ordinarily contain from about 0.5 to about 25% by weight, and preferably from about 1 to about 10% by weight, of the active ingredient in solution. In certain topical and parenteral preparations, various oils are utilized as carriers or excipients. Illustrative of such oils are mineral oils, glyceride oils such as lard oil, cod liver oil, peanut oil, sesame oil, corn oil, and soybean oil. Where a compound is insoluble in the particular vehicle chosen, suspending agents may be added as well as agents to control viscosity of the solution, as for example, magnesium aluminum silicate or carboxymethylcellulose. In addition to these excipients, buffers, preservatives and emulsifying agents may also be suitably employed.

The proportion of the active ingredient employed in parenteral dosage unit forms ranges from about 0.05 to about 20% by weight, preferably from about 0.1 to about 10% by weight of the total liquid composition, the remaining component or components comprising any of the various pharmaceutical excipients previously disclosed. In order to minimize or eliminate irritation at the site of injection, such compositions may contain a non-ionic surfactant having a hydrophile-lipophile balance (HLB) of from about 12 to about 17. The quantity of surfactant in such formulations ranges from about 5 to about 15% by weight. The surfactant can be a single component having the above-identified HLB, or a mixture of two or more components having the desired HLB. Illustrative of surfactants used in parenteral formulations are the class of polyoxyethylene sorbitan fatty acid esters as for example, sorbitan monooleate and the high molecular weight adducts of ethylene oxide with a hydrophobic base, formed by the condensation of propylene oxide with propylene glycol.

The invention herein described is more particularly illustrated in conjunction with the following specific Examples, but not necessarily limited thereto.

EXAMPLE 1

Methyl 2-Hydroxy-5-[1-hydroxy-2-[4-(2-methylphenyl)-1-piperazinyl]ethyl]benzoate Hydrochloride A solution of 10.9 g (0.04 mol) of methyl 5-(2-bromoacetyl)-2-hydroxybenzoate in 100 ml of dry tetrahydrofuran is added dropwise over 4 hours to a stirred solution of 7.1 g (0.04 mol) of 1-(2-methylphenyl)piperazine and 4.0 g (0.04 mol) of triethylamine in 75 ml of tetrahydrofuran at room temperature. Stirring is continued for 2–12 hours or until the theoretical amount (7.3 g) of triethylamine hydrobromide precipitates. The precipitates is removed by filtration and the filtrate is evaporated to dryness. Addition of 2 equivalents of methanolic HCl and precipitation by addition of ethyl ether at room temperature affords the crude methyl 2-hydroxy-5-[2-[4-(2-methylphenyl)-1-piperazinyl]acetyl]benzoate dihydrochloride (9.4 g). Attempts to purify this product by recrystallization frequently led to decomposition and were subsequently avoided.

The crude product is suspended in approximately 300 ml of methanol, the mixture is cooled to 0° C. and 4.8 g (0.126 mol) of sodium borohydride is added during a period of from 10 to 60 minutes. After stirring at 0° C. for an additional 15 to 60 minutes, the mixture is poured on ice, acidified with a 10% acetic acid solution, and made basic with NaHCO$_3$. The desired product is extracted into ethyl acetate or methylene chloride, the extract is washed with water followed by a saturated sodium chloride solution, dried over solid anhydrous magnesium sulfate, and the solvent is evaporated in vacuo. Addition of 2 equivalents of methanolic HCl followed by two recrystallizations from methanol yields 3.1 g of methyl 2-hydroxy-5-[1-hydroxy-2-[4-(2-methylphenyl)-1-piperazinyl]ethyl]benzoate hydrochloride. Vacuum drying over KOH at 80° C. and 0.05 mm Hg results in the loss of one of the two moles of HCl giving the monohydrochloride salt having a m.pt. 226°–227° C. Elemental analysis, infrared, ultraviolet and nuclear magnetic resonance spectra are in agreement with the assigned structure.

Following essentially the same procedure, but substituting 1-[3-(trifluoromethyl)phenyl]piperazine, 1-(4-methoxyphenyl)piperazine, 1-(4-chlorophenyl)piperazine, 1-phenylpiperazine, 1-(2-methoxyphenyl)piperazine, and 1-(2-pyridinyl)piperazine for the 1-(2-methyl phenyl)piperazine above results in the preparation of methyl 2-hydroxy-5-[1-hydroxy-2-[4-[3-(trifluoromethyl)phenyl]-1-piperazinyl]ethyl]benzoate hydrochloride, having a m.pt. 202°–3° C. (dec.), methyl 2-hydroxy-5-[1-hydroxy-2-[4-(4-methoxyphenyl)-1-piperazinyl]ethyl]benzoate hydrochloride, having a m.pt. of 198°–200° C. (dec.), methyl 5-[2-[4-(4-chlorophenyl)-1-piperazinyl]-1-hydroxyethyl]-2-hydroxybenzoate hydrochloride, having a m.pt. of 186°–8° C. (dec.), methyl 2-hydroxy-5-[1-hydroxy-2-(4-phenyl-1-piperazinyl)ethyl]benzoate hydrochloride, having a m.pt. of 197°–9° C. (dec.), methyl 2-hydroxy-5-[1-hydroxy-2-[4-(2-methoxyphenyl)-1-piperazinyl]ethyl]benzoate hydrochloride, having a m.pt. of 208°–9° C. (dec.), and methyl 2-hydroxy-5-[1-hydroxy-2-[4-(2-pyridinyl)-1-piperazinyl]ethyl]benzoate, which is an oil having the following NMR characteristics (CDCl$_3$) δ8.20 (dd, 1, J=2, J'=5 Hz, NC=CH), 7.88 (d, 1, J=2 Hz, COC=CH), 7.3–7.6 (m, 2, arom.), 7.00 (d, 1, J=9 Hz, HOC=CH), 6.5–6.7 (m, 2, arom.), 4.78 (t, 1, J=7 Hz, CHOH), 4.02 (s, 3, OCH$_3$), 3.65 (t, 4, J=5 Hz, CH$_2$NAr), 2.4–2.9 (m, 6, CH$_2$N).

EXAMPLE 2

2-Hydroxy-5-[1-hydroxy-2-[4-(2-methylphenyl)-1-piperazinyl]ethyl]benzamide mono- and dihydrochloride The compound methyl 2-hydroxy-5-[1-hydroxy-2-[4-(2-methylphenyl)-1-piperazinyl]ethyl]benzoate hydrochloride is converted to its free base by treatment with NaHCO$_3$ solution and extraction with methylene chloride. The combined extracts are evaporated in vacuo and the residue is dissolved in anhydrous methanol. The alcohol solution is saturated with gaseous ammonia at 0° C., and a small amount of sodium methoxide or sodium amide, or sodium metal is added as a catalyst. The reaction mixture is permitted to warm to room temperature and is stirred for several days. The reaction is followed by this layer chromatography to determine dissappearance of ester. When the reaction is completed, which in some instances requires addition of more catalyst, the reaction mixture is evaporated to dryness, treated with a 10% acetic acid solution to destroy the catalyst, made basic with NaHCO$_3$ and the desired product is extracted into ethyl acetate or methylene chloride. The combined extracts are washed with water followed by a NaHCO$_3$ solution, dried over anhydrous MgSO$_4$, and the solvent is evaporated in vacuo. The addition of 2 equivalents of methanolic HCl and subsequent recrystallization from methanol or water or mixtures of these two solvents yields 2-hydroxy-5-[1-hydroxy-2-[4-(2-methylphenyl)-1-piperazinyl]ethyl]benzamide dihydrochloride, having a m.pt. 192°–193° C. (dec.), or the monohydrochloride, having a m.pt. 232° C. (dec.). Vacuum drying over KOH at 80° C. and 0.05 mm Hg results in the loss of one of the two moles of HCl. Elemental analysis, infrared, ultraviolet and nuclear magnetic resonance spectra are in agreement with the assigned structure.

Following essentially the same procedure but substituting methyl 2-hydroxy-5-[1-hydroxy-2-[4-[3-(trifluoromethyl)phenyl]-1-piperazinyl]ethyl]benzoate hydrochloride, methyl 2-hydroxy-5-[1-hydroxy-2-[4-(4-methoxyphenyl)-1-piperazinyl]ethyl]benzoate hydrochloride, methyl 5-[2-[4-(4-chlorophenyl)-1-piperazinyl]-1-hydroxyethyl]-2-hydroxybenzoate hydrochloride, methyl 2-hydroxy-5-[1-hydroxy-2-(4-phenyl-1-piperazinyl)ethyl]benzoate hydrochloride, methyl 2-hydroxy-5-[1-hydroxy-2-[4-(2-methoxyphenyl)-1-piperazinyl]ethyl]benzoate hydrochloride and methyl 2-hydroxy-5-[1-hydroxy-2-[4-(2-pyridinyl)-1-piperazinyl)ethyl]benzoate for the methyl 2-hydroxy-5-[1-hydroxy-2-[4-(2-methylphenyl)-1-piperazinyl]ethyl]benzoate hydrochloride above results in the preparation of 2-hydroxy-5-[1-hydroxy-2-[4-[3-(trifluoromethyl)phenyl]-1-piperazinyl]ethyl]benzamide hydrochloride having a m.pt. of 218°–220° C. (dec.), 2-hydroxy-5-

[1-hydroxy-2-[4-(4-methoxyphenyl)-1-piperazinyl]ethyl]benzamide dihydrochloride, having a m.pt. of 207°–8° C. (dec.), 5-[2-[4-(4-chlorophenyl)-1-piperazinyl]-1-hydroxyethyl]-2-hydroxybenzamide monohydrochloride monohydrate, having a m.pt. of 157°–60° C. (dec.), 2-hydroxy-5-[1-hydroxy-2-(4-phenyl-1-piperazinyl)ethyl]benzamide monohydrochloride hydrate, having a m.pt. of 128°–32° C. (dec.), 2-hydroxy-5-[1-hydroxy-2-[4-(2-methoxyphenyl)-1-piperazinyl]ethyl]benzamide monohydrochloride, having a m.pt. of 226°–7° C. (dec.) and 2-hydroxy-5-[1-hydroxy-2-[4-(2-pyridinyl)-1-piperazinyl]ethyl]benzamide monohydrochloride hydrate, having a m.pt. of 219°–20° C. (dec.).

Following essentially the same procedure but substituting methyl 2-hydroxy-5-[1-hydroxy-2-[4-(4-methoxyphenyl)-1-piperazinyl]ethyl]benzoate hydrochloride and methyl 2-hydroxy-5-[1-hydroxy-2-[4-(2-methoxyphenyl)-1-piperazinyl]ethyl]benzoate hydrochloride for the methyl 2-hydroxy-5-[1-hydroxy-2-[4-(2-methylphenyl)-1-piperazinyl]ethyl]benzoate hydrochloride above and using gaseous methylamine in lieu of ammonia results in the preparation of 2-hydroxy-5-[1-hydroxy-2-[4-(4-methoxyphenyl)-1-piperazinyl]ethyl]-N-methylbenzamide monohydrochloride hydrate, having a m.pt. of 188°–9° C. (dec.), and 2-hydroxy-5-[1-hydroxy-2-[4-(2-methoxyphenyl)-1-piperazinyl]ethyl]-N-methylbenzamide monohydrochloride monohydrate, having a m.pt. of 162°–5° C. (dec.), respectively.

EXAMPLE 3

N-(2,2-Dimethylpropyl)-2-hydroxy-5-[1-hydroxy-2-[4-(2-methylphenyl)-1-piperazinyl]ethyl]benzamide Monohydrochloride To 40 ml of methanol under nitrogen is added approximately 200 mg of metallic sodium. After the reaction subsides 5.2 g (0.014 mol) of methyl 2-hydroxy-5-[1-hydroxy-2-[4-(2-methylphenyl)-1-piperazinyl]ethyl]benzoate is added thereto followed by 40 ml of neopentylamine. The mixture is stirred at room temperature for 4 days. The solution is evaporated to dryness under vacuum. The residue is dissolved in ethyl acetate and the solution is filtered to remove insolubles. The filtrate is washed with NaHCO$_3$ solution, dried over anhydrous MgSO$_4$, which is removed by filtration, and the solvent is evaporated in vacuo. Addition of methanolic HCl and recrystallization from methanol, yields N-(2,2-dimethylpropyl)-2-hydroxy-5-[1-hydroxy-2-[4-(2-methylphenyl)-1-piperazinyl]ethyl]benzamide monohydrochloride, having a m.pt. of 239°–40° C. (dec.).

Following essentially the same procedure but substituting dodecylamine for the neopentylamine above results in the preparation of N-dodecyl-2-hydroxy-5-[1-hydroxy-2-[4-(2-methylphenyl)-1-piperazinyl]ethyl]benzamide hydrochloride.

EXAMPLE 4

Methyl 5-[1-Hydroxy-2-(4-phenyl-1-piperazinyl)ethyl]-2-methoxybenzoate Hydrochloride A solution of 15.0 g (0.0522 mol) of methyl 5-(bromoacetyl)-2-methoxybenzoate in 500 ml of anhydrous tetrahydrofuran is added dropwise over 2–4 hours to a solution of 8.48 g (0.0522 mol) of 1-phenylpiperazine and 5.28 g (0.0522 mol) of triethylamine in 100 ml of tetrahydrofuran. The mixture is stirred at room temperature under exclusion of moisture overnight. The precipitated triethylamine hydrobromide is removed by filtration and the filtrate is evaporated to dryness. Addition of 2 equivalents of methanolic HCl and precipitation by addition of ethyl ether yields crude 2-methoxy-5-[2-(4-phenyl-1-piperazinyl)acetyl]benzoate hydrochloride (21.0 g) that can be used without further purification.

This material is dissolved in 800 ml of methanol, the solution is cooled in an ice-salt bath and 11.78 g (0.3114 mol) of sodium borohydride is added portionwise at such a rate as to keep the reaction temperature below 0° C. (approximately 45 minutes). The reaction mixture is stirred for an additional 30 minutes, poured on ice, acidified with 10% solution of acetic acid, and made basic with NaHCO$_3$. The desired product is extracted into methylene chloride. The combined extracts are washed with water and NaHCO$_3$ solution, dried over anhydrous MgSO$_4$ which is removed by filtration, and the solvent is evaporated in vacuo. Addition of 2 equivalents of methanolic HCl and precipitation from ethyl ether yields methyl 5-[1-hydroxy-2-(4-phenyl-1-piperazinyl)ethyl]-2-methoxybenzoate hydrochloride, having a m.pt. of 196°–7° C. (dec.).

Following essentially the same procedure but substituting 1-(2-methoxyphenyl)piperazine and 1-(2-methylphenyl)piperazine for the 1-phenylpiperazine above results in the preparation of methyl 5-[1-hydroxy-2-[4-(2-methoxyphenyl)-1-piperazinyl]ethyl]-2-methoxybenzoate hydrochloride, having a m.pt. of 198°–200° C. (dec.), and methyl 5-[1-hydroxy-2-[4-(2-methylphenyl)-1-piperazinyl]ethyl]-2-methoxybenzoate hydrochloride, having a m.pt. of 218°–20° C. (dec.), respectively.

EXAMPLE 5

5-[1-Hydroxy-2-(4-phenyl-1-piperazinyl)ethyl]-2-methoxybenzamide Hydrochloride The compound methyl 5-[1-hydroxy-2-(4-phenyl-1-piperazinyl)ethyl]-2-methoxybenzoate (10.0 g) is converted to its free base by treatment with NaHCO$_3$ solution and extraction with methylene chloride. The extract is evaporated to dryness in vacuo and the residue is suspended in 200 ml of anhydrous methanol, cooled to 0° C., and gaseous ammonia is bubbled in to saturation. A small amount (approximately 200 mg) of sodium methoxide is added and the mixture is stirred at room temperature for several days until all of the ester is converted to the amide, as determined by thin layer chromatography. The solvent is evaporated in vacuo and the residue is treated with water and ethyl acetate. Some of the desired product is collected by filtration and the remainder is recovered from the organic solvent (6.9 g). Two equivalents of methanolic HCl are added and the salt is recrystallized from a mixture of ethyl acetate and methanol. The product is vacuum dried at 80° C. over KOH at 0.05 mm Hg to yield 5-[1-hydroxy-2-(4-phenyl-1-piperazinyl)ethyl]-2-methoxybenzamide monohydrochloride, having a m.pt. of 235°–6° C. (dec.).

Following essentially the same procedure but substituting methyl 5-[1-hydroxy-2-[4-(2-methoxyphenyl)-1-piperazinyl]ethyl]-2-methoxybenzoate hydrochloride and methyl 5-[1-hydroxy-2-[4-(2-methylphenyl)-1-piperazinyl]ethyl]-2-methoxybenzoate hydrochloride for the methyl-5-[1-hydroxy-2-(4-phenyl-1-piperazinyl)ethyl]-2-methoxybenzoate above results in the preparation of 5-[1-hydroxy-2-[4-(2-methoxyphenyl)-1-piperazinyl]ethyl]-2-methoxybenzamide hydrochloride, having a m.pt. of 247°–8° C. (dec.) and 5-[1-hydroxy-2-[4-(2-methylphenyl)-1-piperazinyl]ethyl]-2-methoxybenzamide hydrochloride, having a m.pt. of 214°–6° C. (dec.), respectively.

EXAMPLE 6

5-[1-Hydroxy-2-[4-(2-methoxyphenyl)-1-piperazinyl]ethyl]-2-methoxy-N-methylbenzamide Hydrochloride The compound methyl 5-[1-hydroxy-2-[4-(2-methoxyphenyl)-1-piperazinyl]ethyl]-2-methoxybenzoate hydrochloride (8.0 g) is converted to its free base by treatment with a solution of 2 Normal NaOH and extracted with methylene chloride. The combined extracts are evaporated to dryness in vacuo, dissolved in 50 ml of methanol and added to 250 ml of methanol to which a small piece (about 100 mg) of metallic sodium has been added to form sodium methoxide. The resulting solution is cooled in an ice-methanol bath and saturated with gaseous methylamine (21.0 g). The reaction mixture is stirred at room temperature until thin layer chromatography indicates that amide formation is complete (7 days). The solvent is evaporated to dryness in vacuo, and the residue is dissolved in ethyl acetate. The ethyl acetate solution is washed with water, dried over anhydrous $MgSO_4$ which is removed by filtration, and the solvent is evaporated in vacuo. Two equivalents of methanolic HCl are added and the desired compound is crystallized from methanol. Recrystallization from an isopropanol-water mixture and vacuum drying at 80° C. yields 5-[1-hydroxy-2-[4-(2-methoxyphenyl)-1-piperazinyl]ethyl]-2-methoxy-N-methylbenzamide hydrochloride, having a m.pt. of 218°–9° C. (dec.).

Following essentially the same procedure but substituting methyl 5-[1-hydroxy-2-[4-(2-methylphenyl)-1-piperazinyl]ethyl]-2-methoxybenzoate hydrochloride for the methyl 5-[1-hydroxy-2-[4-(2-methoxyphenyl)-1-piperazinyl]ethyl]-2-methoxybenzoate hydrochloride above results in the preparation of 5-[1-hydroxy-2-[4-(2-methylphenyl)-1-piperazinyl]ethyl]-2-methoxy-N-methylbenzamide hydrochloride, having a m.pt. of 226°–7° C. (dec.).

EXAMPLE 7

2-Ethoxy-5-[1-hydroxy-2-(4-phenyl-1-piperazinyl)ethyl]benzamide Hydrochloride

A mixture of 169.0 g (0.875 mol) of methyl 5-acetyl-2-hydroxybenzoate, 205.0 g (1.31 mol) of ethyl iodide and 121.0 g (0.875 mol) of $K_2CO_3$ in 500 ml of dimethylformamide is stirred at room temperature for 45 hours. The mixture is poured into 1.8 l of ice-water and extracted four times with methylene chloride. The combined extracts are washed with water, followed by a 2 N $Na_2CO_3$ solution, a saturated sodium chloride solution, dried over sodium sulfate, and the solvent is evaporated to dryness in vacuo. The resulting oil is dissolved in ether and upon the addition of pentane the methyl 5-acetyl-2-ethoxybenzoate crystallizes, m.pt. 47°–50° C., 147 g (76%).

To a solution of 144.0 g (0.65 mol) of this compound dissolved in 800 ml of chloroform is added via dropwise addition a solution of 104.0 g (0.65 mol) of bromine dissolved in 300 ml of chloroform, as fast as the decoloration of bromine occurs (1 hour after an initiation period of 1.5 hours). The solvent is evaporated in vacuo and the residue recrystallized from a mixture of methanol-acetone to yield 100 g (51%) of methyl 5-(2-bromoacetyl)-2-ethoxybenzoate, m.pt. 147°–8° C. A second crop of crystals is obtained from the mother liquor.

A solution of 15.0 g (0.0498 mol) of this bromoketone dissolved in 550 ml of dry tetrahydrofuran is added via dropwise addition over a period of 4 hours to a solution of 8.1 g (0.0498 mol) of 1-phenylpiperazine and 5.0 g (0.048 mol) of triethylamine dissolved in 100 ml of tetrahydrofuran at 25° C. The reaction mixture is stirred at 25° C. overnight. The precipitated triethylamine hydrobromide is removed via filtration and the filtrate is evaporated to dryness in vacuo. Two equivalents of methanolic HCl are added and the crude methyl 5-[2-(4-phenylpiperazin-1-yl)acetyl]-2-ethoxybenzoate hydrochloride crystallizes from solution. This material (17.8 g) is dissolved in 500 ml of methanol, the solution is cooled in an ice-salt bath and 9.65 g of sodium borohydride is added in portions while maintaining the reaction temperature below 0° C. After addition is complete (45 minutes) the mixture is stirred for another 30 minutes and poured on ice. The reaction mixture is acidified with a 10% acetic acid solution (1 l) made basic with $NaHCO_3$ and extracted with methylene chloride. The combined extracts are washed with water and dried over anhydrous $MgSO_4$, which is removed via filtration. The solvent is evaporated in vacuo leaving 14.4 g of crude methyl 2-ethoxy-5-[1-hydroxy-2-(4-phenylpiperazin-1-yl)ethyl]benzoate.

Following essentially the procedure of Example 5, the compound is treated with ammonia in the manner described to yield 6.4 g of 2-ethoxy-5-[1-hydroxy-2-(4-phenyl-1-piperazinyl)ethyl]benzamide hydrochloride, having a m.pt. of 208°–10° C. (dec.).

EXAMPLE 8

α-(4-Hydroxy-3-1H-tetrazol-5-ylphenyl)-4-(2-methylphenyl)-1-piperazineethanol Monohydrochloride Monohydrate A suspension of 16.2 g (0.1 mol) of 5-(2-hydroxyphenyl)-1H-tetrazole in 300 ml of dry methylene chloride is cooled in an ice bath, 39.9 g (0.3 mol) of anhydrous aluminum chloride are added and acetyl chloride 8.1 g (0.1 mol) is added via dropwise addition over a period of 5 minutes. The mixture is refluxed for 3.5 hours, cooled, and 200 ml of 2N HCl is added dropwise with stirring. The resulting precipitate is collected, washed with 2N HCl, water and recrystallized from an isopropanol-water mixture to yield 8.0 g of 1-[4-hydroxy-3-(1H-tetrazol-5-yl)phenyl]ethanone, m.pt. 260°–261° C. (dec.).

To a solution of 6.9 g (0.034 mol) of this compound in 800 ml of refluxing tetrahydrofuran is added 15.2 g (0.068 mol) of cupric bromide in six portions over a period of 2 hours. The mixture is refluxed for 2 hours and concentrated to a volume of about 100 ml. Cuprous bromide is removed via filtration and chloroform added to the filtrate until 2-bromo-1-[4-hydroxy-3(1H-tetrazol-5-yl)phenyl]ethanone crystallizes from solution, 8.2 g (84%), m.pt. 177°–178° C. (dec.).

A solution of 12.0 g (0.0424 mol) of this compound in 650 ml of anhydrous tetrahydrofuran is added over a period of 1.5 hours to a stirred solution of 7.5 g (0.0424 mol) of 1-(2-methylphenyl)piperazine and 8.6 g (0.0848 mol) of triethylamine contained in 300 ml of tetrahydrofuran at 25° C. The reaction mixture is stirred at 25° C. for 3 days. The resulting precipitate is collected. One equivalent of methanolic HCl is added to the filtrate to provide another precipitate that is also collected. The combined precipitates are treated with NaHCO₃ solution and extracted with methylene chloride and ethyl acetate. The combined organic extracts are washed with water, dried over MgSO₄ and the solvent evaporated to dryness in vacuo. The residue (12.7 g) is dissolved in 400 ml of methanol, the solution cooled to below 0° C. and 7.6 g (0.2 mol) of sodium borohydride is added in portions while maintaining the temperature below 0° C. After completed addition (45 minutes) the mixture is stirred for approximately 30 minutes at 0° C. The reaction is quenched by the addition of 500 ml of 10% acetic acid solution. The mixture is made basic by addition of NaHCO₃, and the product is extracted into methylene chloride. The combined methylene chloride extracts are washed with water, dried over MgSO₄ which is removed by filtration, and the solvent is evaporated in vacuo. Two equivalents of methanolic HCl are added to the residue. The title compound crystallizes slowly, is recrystallized from methanol, vacuum dried at 80° C. and has a m.pt. 186°–188° C. (dec.). Elemental analysis and spectra of this compound are in agreement with the assigned structure.

EXAMPLE 9

The following Example is illustrative of the α and β-adrenergic blocking activity and the direct spasmolytic activity for the compounds of this invention.

α-Adrenergic receptor blocking activity is determined in vitro by performing cumulative dose-response experiments in the isolated rabbit aortic strip preparation using norepinephrine as the agonist. The contractile response of the rabbit strip preparation in the presence of logarithmically increasing concentrations of the compounds being tested are expressed as percent of the maximal attainable aqueous. Relative antagonistic potency is expressed as a $pA_2$ value. The $pA_2$ is defined as the negative logarithm of the concentration of the antagonist which produces a doubling of the concentration of agonist required to produce a 50% maximal contraction. The resulting $pA_2$ values for several of the compounds of this invention are shown in Table 1 below.

β-Adrenergic receptor blocking activity is determined in vitro by performing cumulative dose-response experiments in the isolated guinea pig atria preparation using isoproterenol as the agonist. The response (increase in rate) of the guinea pig atria preparation in the presence of logarithmically increasing concentrations of the compounds being tested are expressed as percent of the maximal attainable response. Relative antagonistic potency is expressed as a $pA_2$ value, as defined above. The $pA_2$ values for various compounds of this invention are shown below in Table 1.

Direct spasmolytic activity is determined in vitro by performing cumulative dose response experiments in the isolated guinea pig ileum preparation using barium chloride as the agonist. The contractile response of the guinea pig ileum preparation in the presence of logarithmically increasing concentrations of the compounds being tested are expressed as percent of the maximal attainable response. Relative antagonistic potency is expressed as a $pA_2$ value, as defined above.

The $pA_2$ values for various compounds of this invention are shown below in Table 1.

TABLE 1
In vitro α-and β-Adrenergic Blocking and Direct Spasmolytic Activity

| Compound | $pA_2$ α | $pA_2$ β | $BaCl_2$ |
|---|---|---|---|
| 1 | 7.45 | 6.79 | 6.06 |
| 2 | 7.57 | 6.70 | 5.73 |
| 3 | 6.33 | 6.90 | 5.74 |
| 4 | 6.13 | 5.84 | <4.28 |
| 5 | 6.87 | 6.17 | 4.58 |
| 6 | 7.04 | (stimulant) | 4.19 |
| 7 | 7.42 | 6.44 | 4.87 |
| 8 | 6.08 | 5.37 | 3.90 |
| 9 | 5.47 | 5.17 | 4.82 |
| 10 | 7.95 | (stimulant) | 5.02 |
| 11 | 7.21 | 6.33 | 6.65 |
| 12 | 6.54 | <5 | 4.19 |
| 13 | 6.27 | 5.27 | 4.67 |
| 14 | 7.56 | 6.14 | <4 |
| phentolamine | 7.78 | <5 | 5.70 |
| propranolol | <5 | 8.89 | 5.75 |
| nylidrine | 6.21 | (stimulant) | 5.37 |

| Compound No. | |
|---|---|
| 1 | methyl 2-hydroxy-5-[1-hydroxy-2-[4-(2-methylphenyl)-1-piperazinyl]ethyl]benzoate hydrochloride. |
| 2 | 2-hydroxy-5-[1-hydroxy-2-[4-(2-methylphenyl)-1-piperazinyl]ethyl]benzamide monohydrochloride. |
| 3 | 2-hydroxy-5-[1-hydroxy-2-[4-[3-(trifluoromethyl)phenyl]-1-piperazinyl]ethyl]benzamide monohydrochloride. |
| 4 | 2-hydroxy-5-[1-hydroxy-2-[4-(4-methoxyphenyl)-1-piperazinyl]ethyl]benzamide dihydrochloride. |
| 5 | 5-[2-[4-(4-chlorophenyl)-1-piperazinyl]-1-hydroxyethyl]-2-hydroxybenzamide monohydrochloride, monohydrate. |
| 6 | 2-hydroxy-5-[1-hydroxy-2-(4-phenyl-1-piperazinyl)ethyl]benzamide monohydrochloride hydrate. |
| 7 | 2-hydroxy-5-[1-hydroxy-2-[4-(2-methoxyphenyl)-1-piperazinyl]ethyl]benzamide monohydrochloride. |
| 8 | 2-hydroxy-5-[1-hydroxy-2-[4-(2-pyridinyl)-1-piperazinyl]ethyl]benzamide monohydrochloride hydrate. |
| 9 | 2-hydroxy-5-[1-hydroxy-2-[4-(4-methoxyphenyl)-1-piperazinyl]ethyl]-N-methylbenzamide monohydrochloride hydrate. |
| 10 | 2-hydroxy-5-[1-hydroxy-2-[4-(2-methoxyphenyl)-1-piperazinyl]ethyl]-N-methylbenzamide monohydrochloride monohydrate. |
| 11 | N-(2,2-dimethylpropyl)-2-hydroxy-5-[1-hydroxy-2-[4-(2-methylphenyl)-1-piperazinyl]ethyl]benzamide monohydrochloride. |
| 12 | 5-[1-hydroxy-2-(4-phenyl-1-piperazinyl)ethyl]-2-methoxybenzamide monohydrochloride. |
| 13 | 2-ethoxy-5-[1-hydroxy-2-(4-phenyl-1-piperazinyl)ethyl]benzamide monohydrochloride. |
| 14 | α-(4-hydroxy-3-1H-tetrzol-5-yl-phenyl)-4-(2-methylphenyl)-1-piperazineethanol monohydrochloride monohydrate. |

EXAMPLE 10

The following Example illustrates the in vivo α and β-adrenergic blocking activity for the compounds of this invention.

α-Adrenergic receptor blocking activity is determined in vivo by performing cumulative dose-response experiments in the anesthetized dog using phenylephrine as the agonist. The increase in diastolic blood pressure produced by phenylephrine is determined in the absence and again in the presence of logarithmically increasing doses of the test compound. Relative antagonistic potency is expressed as $DR_{10}$. $DR_{10}$ is defined as the negative logarithm of the dose of the antagonist which increased by 10 times the dose of agonist necessary to produce 50% of the maximal attainable response. The compound 2-hydroxy-5-[1-hydroxy-2-[4-(2-methylphenyl)-1-piperazinyl]ethyl]benzamide monohydrochloride produces a $DR_{10}$ of 1.09 mg/kg iv. By comparison, phentolamine, a known α-blocker demonstrates a $DR_{10}$ of 2.65 mg/kg iv.

β-Adrenergic receptor blocking activity is determined in vivo similarly using isoproterenal as the agonist. Two responses, increase in cardiac rate ($\beta_1$) and decrease in diastolic blood pressure ($\beta_2$) are measured. The compound 2-hydroxy-5-[1-hydroxy-2-[4-(2-methylphenyl)-1-piperazinyl]ethyl]benzamide monohydrochloride produces a $DR_{10}$ of 15.3 mg/kg iv ($\beta_1$) and >>10 mg/kg iv ($\beta_2$), respectively. The reference compound propranolol demonstrates a $DR_{10}$ of 0.55 ($\beta_1$) and 0.26 ($\beta_2$) mg/kg iv, respectively.

EXAMPLE 11

The following Example illustrates the antihypertensive activity for the compounds of this invention.

Antihypertensive activity is determined in spontaneously hypertensive rats (SHR) of the Okomoto-Aoki strain. Systolic blood pressure of the SHR is measured from the caudal artery by means of an indirect method utilizing a photocell transducer/tail cuff occluder system. Time response relationships are determined for each compound following an oral dose of 50 mg/kg. Data are expressed as mm of Hg decrease from control values. Statistical significance is determined using a 2 tailed "t" test comparing drug treatment response values to those obtained from concurrent vehicle treated animals. The results obtained are illustrated in Table II.

TABLE II

| Antihypertensive Activity in SHR after 50 mg/kg per os. | | |
|---|---|---|
| Compound Described in Example No. | Fall in Blood Pressure After: 1 hour | 4 hours(mm Hg) |
| 1 | 48 | 37 |
| 2 | 49 | 56 |
| 3 | 45 | 35 |
| 4 | 44 | 52 |
| 5 | 41 | 32 |
| 6 | 33 | 25 |
| 7 | 48 | |

| Compound No. | |
|---|---|
| 1 | 2-hydroxy-5-[1-hydroxy-2-[4-(2-methylphenyl)-1-piperazinyl]ethyl]benzamide monohydrochloride. |
| 2 | 5-[2-[4-(4-chlorophenyl)-1-piperazinyl]-1-hydroxyethyl]-2-hydroxybenzamide monohydrochloride, monohydrate. |
| 3 | 2-hydroxy-5-[1-hydroxy-2-[4-(2-methoxyphenyl)-1-piperazinyl]ethyl]benzamide monohydrochloride. |
| 4 | 2-hydroxy-5-[1-hydroxy-2-[4-(2-methoxyphenyl)-1-piperazinyl]ethyl]-N-methylbenzamide monohydrochloride monohydrate. |

TABLE II-continued

| Antihypertensive Activity in SHR after 50 mg/kg per os. | |
|---|---|
| 5 | N-(2,2-dimethylpropyl)-2-hydroxy-5-[1-hydroxy-2-[4-(2-methylphenyl)-1-piperazinyl]ethyl]-benzamide monohydrochloride. |
| 6 | 5-[1-hydroxy-2-(4-phenyl-1-piperazinyl)ethyl]-2-methoxybenzamide monohydrochloride. |
| 7 | α-(4-hydroxy-3-1H-tetrazol-5-yl-phenyl)-4-(2-methylphenyl)-1-piperazineethanol monohydrochloride monohydrate. |

We claim:
1. A derivative of 2-hydroxy-5-(1-hydroxy-2-piperazinylethyl)benzoic acid having the formula

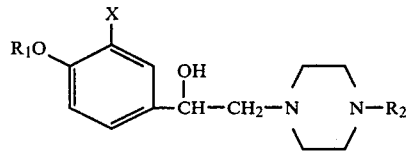

wherein
X is selected from the group consisting of carboxy, carbomethoxy, carboxamide, N-alkylcarboxamide in which the alkyl group has from 1 to 12 carbon atoms, N,N-dimethylcarboxamide, N,N-diethylcarboxamide and 5-tetrazolyl;
$R_1$ is hydrogen, methyl and ethyl;
$R_2$ is selected from the group consisting of phenyl, substituted phenyl, 2-pyridyl and substituted-2-pyridyl in which said substitution is lower alkyl and lower alkoxy having from 1 to 4 carbon atoms, fluorine, chlorine and trifluoromethyl;
and the pharmaceutically acceptable acid addition salts thereof.

2. A compound according to claim 1 wherein X is carboxamide, N-alkylcarboxamide in which the alkyl group has from 1 to 12 carbon atoms, N,N-dimethylcarboxamide and N,N-diethylcarboxamide; and $R_2$ is a methyl substituted phenyl and a methoxy substituted phenyl group.

3. A compound according to claim 1 wherein X is carboxamide; $R_1$ is hydrogen; and $R_2$ is an o-methyl substituted phenyl and an o-methoxy substituted phenyl group.

4. A compound of claim 1 which is 2-hydroxy-5-[1-hydroxy-2-[4-(2-methylphenyl)-1-piperazinyl]ethyl]-benzamide and its pharmaceutically acceptable acid addition salts.

5. A compound of claim 1 which is 2-hydroxy-5-[1-hydroxy-2-[4-(2-methoxyphenyl)-1-piperazinyl]ethyl]-benzamide and its pharmaceutically acceptable acid addition salts.

6. A compound of claim 1 which is 5-[1-hydroxy-2-[4-(2-methoxyphenyl)-1-piperazinyl]ethyl]-2-methoxybenzamide and its pharmaceutically acceptable acid addition salts.

* * * * *